United States Patent
Mane et al.

(10) Patent No.: US 12,274,278 B2
(45) Date of Patent: Apr. 15, 2025

(54) ANTHOCYANIN-BASED COLORANT

(71) Applicant: Chr. Hansen Natural Colors A/S, Hoersholm (DK)

(72) Inventors: Carine Mane, Montpellier (FR); Céline Chanforan, Bouillargues (FR); Patrick Lemmonier, Maugio (FR); Eric Jouenne, Teyran (FR)

(73) Assignee: Chr. Hansen Natural Colors A/S, Hoersholm (DK)

( * ) Notice: Subject to any disclaimer, the term of this patent is extended or adjusted under 35 U.S.C. 154(b) by 914 days.

(21) Appl. No.: 16/746,532

(22) Filed: Jan. 17, 2020

(65) Prior Publication Data

US 2020/0253237 A1 Aug. 13, 2020

Related U.S. Application Data

(62) Division of application No. 14/359,978, filed as application No. PCT/EP2012/073812 on Nov. 28, 2012, now abandoned.

(30) Foreign Application Priority Data

Nov. 28, 2011 (EP) .................... 11190972

(51) Int. Cl.
*A23G 9/42* (2006.01)
*A23G 3/48* (2006.01)
(Continued)

(52) U.S. Cl.
CPC ............ *A23G 9/42* (2013.01); *A23G 3/48* (2013.01); *A23L 2/58* (2013.01); *A23L 5/43* (2016.08); *A23L 19/00* (2016.08); *C09B 61/00* (2013.01)

(58) Field of Classification Search
CPC .... A23G 9/42; A23G 3/48; A23L 5/43; A23L 19/00; A23L 2/58; C09B 61/00
See application file for complete search history.

(56) References Cited

U.S. PATENT DOCUMENTS

| 4,172,902 A | 10/1979 | Asen et al. |
| 4,320,009 A | 3/1982 | Hilton et al. |

(Continued)

FOREIGN PATENT DOCUMENTS

| EP | 1 191 071 | 3/2002 |
| WO | WO 02/17945 A1 | 3/2002 |

OTHER PUBLICATIONS

Cipriano, Improved Extraction of Acylated Anthocyanins From Purple Sweet Potato (*Ipomoea Batata*) for Enhanced Antiinflammatory Activity and Their Metabolite Production During Porcine Fecal Digestion, A Dissertation by Paula De Aguiar Ciprian, Submitted to the Office of Graduate and Professional Studies of Texas.*

(Continued)

*Primary Examiner* — Donald R Spamer
*Assistant Examiner* — Philip A Dubois
(74) *Attorney, Agent, or Firm* — Jerold I. Schneider; SCHNEIDER IP LAW

(57) ABSTRACT

1. A composition, which is an anthocyanin-based colorant composition comprising 50-90 mol-%, based on the total amount of anthocyanins, of pelargonidin-based anthocyanins, and wherein (i) >70 mol-% of all anthocyanins are acylated with at least one phenolic acid; and (ii) >20 mol-% of all anthocyanins are acylated with at least one hydroxycinnamic acid; and wherein the composition has a red color with a hue value H≥ in the L*C*h* color system in the range of 10-30, measured at an L*-value of (70.0±0.1) in a 0.1 mol/l trisodium citrate dihydrate buffer at pH 3 in a 1 cm-length quartz cell using Spectraflash 650 (Datacolor) in transmission mode under D65 illuminant 10 Deg. Also, the (Continued)

present invention relates to use of the above compositions as a food colorant.

13 Claims, 6 Drawing Sheets

(51) Int. Cl.
  *A23L 2/58* (2006.01)
  *A23L 5/43* (2016.01)
  *A23L 19/00* (2016.01)
  *C09B 61/00* (2006.01)

(56) References Cited

U.S. PATENT DOCUMENTS

| | | |
|---|---|---|
| 6,180,154 B1 | 1/2001 | Wrolstad et al. |
| 2008/0313822 A1 | 12/2008 | Bertoldo De Barros et al. |
| 2008/0319053 A1 | 12/2008 | Barros et al. |
| 2009/0324787 A2 | 9/2009 | Koji |
| 2015/0017303 A1 | 1/2015 | Mane et al. |

OTHER PUBLICATIONS

Asen et al., "Co-pigmentation of anthocyanins in plant tissues and its effect on color," Phytochemistry. Mar. 1972; 11(3): 1139-44.
Bakowska-Barczak, "Acylated anthocyanins as stable, natural food colorants—a review," Pol J Food Nutr Sci 2005; 14(2):107-116.
Bassa, I.A., Francis, F.J. 1987. "Stability of Anthocyanins from Sweet Potatoes in a Model Beverage." J. Food Sci. vol. 52, pp. 1753-1754.
Celvallos-Casals, B.A., Cisneros-Zevallos, L. 2004. "Stability of anthocyanin-based aqueous extract of Andean purple corn and red-fleshed sweet potato compared to synthetic and natural colorants." Food Chem. vol. 86, pp. 69-77.
Dangles et al., "Anthocyanin intramolecular copigment effect," Phytochemistry. Aug. 1993; 34(1): 119-24.
Figueiredo et al., "New features of intramolecular copigmentation byacylated anthocyanins," Phytochemistry. May 1999; 51 (1):125-32.
Guisti, M.M., Rodriguez-Saona, L.E., Wrolstad, R.E. 1999. "Molar Absorptivity and Color Characteristics of Acylated and Non-Acylated Pelargonidin-Based Anthocyanins," J. Agric. Food Chem. vol. 47, pp. 4631-4637.
Imbert, M.P., Seaforth, C.E., Williams, D.B. 1966. "The Anthocyanin Pigments of the Sweet potato *Ipomoea batatas* (L.) *Lam*." American Society for Horticultural Science. vol. 88, pp. 481-485.
International Search Report and Written Opinion for PCT/EP2012/073812, mailed Jan. 25, 2013.
Lee, M.J., Park, J.S., Choi, D.S., Jung, M.Y. 2013. "Characterization and Quantitation of Anthocyanins in Purple-Fleshed Sweet Potatoes Cultivated in Korea by HPLC-DAD and HPLC-ESI-QTOF-MS/MS." J. Agric. Food Chem. vol. 61, pp. 3148-3158.
Mazza et al., "Recent developments in the stabilization of anthocyanins in food products," Food Chemistry. 1987; 25(3):207-25.
Office Action issued on Feb. 10, 2017, in U.S. Appl. No. 14/359,978 (US 2015-0017303).
Office Action issued on Jul. 19, 2018, in U.S. Appl. No. 14/359,978 (US 2015-0017303).
Office Action issued on Sep. 7, 2017, in U.S. Appl. No. 14/359,978 (US 2015-0017303).
Otsuki et al., "Acylated anthocyanins from red radish (*Raphanus sativus* L.)," Phytochemistry. May 2002; 60(1):79-87.
Rodriguez-Saona et al., "Anthocyanin Pigment Composition of Red-fleshed Potatoes," Journal of Food Science. May 1, 1998; 63(3):458-65.
Saito et al., "Acylated pelargonidin 3,7-glycosides from red flowers of Delphinium hybridum," Phytochemistry. Oct. 1998; 49(3):88 I-86.
Shi, Z., Bassa, I.A., Gabriel, S.L., Francis, F.J. 1992. "Anthocyanin Pigments of Sweet Potatoes *Ipomoea batatas*," J. Food Sci. vol. 57, pp. 755-757, 770.
Terahara et al., "Functional new acylated sophoroses and deglucosylated anthocyanins in a fermented red vinegar," J Agric Food Chem. Sep. 23, 2009; 57(18):8331-8. doi: 10.1021/jf901809p.
Tian, Q., Konczak, I., Schwartz, S.J. 2005. "Probing Anthocyanin Profiles in Purple Sweet Potato Cell Line (*Ipomoea batatas* L. Cv. *Ayamurasaki*) by High-Performance Liquid Chromatography and Electrospray Ionization Tandem Mass Spectrometry." J. Agric. Food Chem. vol. 53, pp. 6503-6509.
Truong, V.-D., Deighton, N., Thompson, R.T., McFeeters, R.F., Dean, L.O., Pecota, K.V., Yencho, G.C. 2010. "Characterization of Anthocyanins and Anthocyanidins in Purple-Fleshed Sweetpotatoes by HPLC-DAD/ESI-MS/MS." J. Agric. Food Chem. vol. 58, pp. 404-41 0.
Office Action issued on Dec. 27, 2018, in U.S. Appl. No. 14/359,978 (US 2015-0017303).
Office Action issued on Sep. 18, 2019 in U.S. Appl. No. 14/359,978 (US 2015-0017303).
Manual Tecnico Del Cultivo De Camote, Ecuadorian Ministry of Agriculture, 2017.
Drapal et al, Horticulture Research 2019 6:20 OI 10.1038/s41438-018-0075-5.

* cited by examiner

ANTHOCYANIN-BASED COLORANT

CROSS-REFERENCE TO RELATED APPLICATIONS

This application is a divisional of U.S. application Ser. No. 14/359,978, filed May 22, 2014, which is the U.S. national stage under 35 U.S.C. § 371 of international application, PCT/EP2012/073812, filed Nov. 28, 2012, which claims priority to European patent application 11190972.7, filed Nov. 28, 2011, each of which is incorporated herein by reference.

FIELD OF INVENTION

The present invention relates to the technical field of natural colorants, especially food colorants, which can be obtained from plant extracts, and further relates to the use of these colorants for food coloring.

BACKGROUND

Colorants containing natural coloring substances are commonly used in the manufacturing of e.g. food products and pharmaceutical products. However, there are increasingly strict requirements to be fulfilled for natural colorants to be accepted as a commercial coloring agent especially in the field of coloring food products, sweets and pharmaceuticals.

First of all, a colorant must be stable under common use conditions. This means that in many food applications a colorant must be thermally stable against heat exposure occurring on the occasion of e.g. food pasteurization prior to packaging or heating by the consumer prior to consumption. Also, the colorants must show sufficient photostability, i.e. they must be stable against light exposure over the lifetime of the colored (food) product without substantial color change or disappearance (fading).

Even further, the colorant must be stable against chemical interaction with other compounds in the environment of food. As many food products have a pH in the acidic range, this means that the colorant must be stable in media having a low pH. This especially applies in the case of beverages, which have a relatively low pH in the range of 2.0-4.5, and more commonly 2.5-3.6. For example, fruit preparations usually have a pH in the range 3.6-4.3 and more commonly 3.9-4.1 and in yoghurts usually have a pH in the range 4.1-4.7.

In addition, the colorant itself may not have a strong taste and/or odor in itself. However, depending on the origin of the natural colorant, a colorant sometimes can have a strong taste and/or odor in itself, which would render it unsuitable as a colorant for certain (food) products. This is the case for colorant produced from red radish or red cabbage.

Anthocyanins are well known as a group of compounds giving color to food, vegetables and flowers and are responsible for the blue, purple, violet, magenta, red and orange color of many plant species. Anthocyanins are water soluble, non-toxic pigments and therefore anthocyanins extracted from fruit and vegetables have been used as food colorants for providing colors in the orange to purple color range.

Despite the known utility of natural food colorants including anthocyanin food colorants, there exists a desire to develop a greater diversity of color tones suitable for commercial colorants. Also, especially for coloring foods such as beverages, dairy, ice cream and confectionary, colorants having a high brightness thus providing a clear and distinct color tone, especially such a red color tone, are desirable.

SUMMARY OF THE INVENTION

In view of the foregoing, the problem underlying the present invention resides in the provision of a new natural red-orange colorant especially suitable for food coloring, which is at least as stable as the known anthocyanin food colorants, has a high brightness and has a clear and distinct color tone. In a preferred embodiment, the red-orange color tone obtained is clearly different from the color tone of most other red anthocyanin colorants. Also, the colorant should be free of off-tastes or off-odors which would make it unsuitable for use in food coloring applications, such as beverages. Red-orange color tones can also be obtained using other colorants, such as carminic acid or red radish extracts. However, carminic acid is obtained from an animal source (bugs) and thus is not suitable for vegetarian consumers. Red radish is problematic as it contains sulfur compounds and thus has an undesirable characteristic smell and taste.

As a result of the inventors' comprehensive research undertaken in an attempt to solve the above problem, it has been surprisingly found that such a desirable colorant can be obtained by providing compositions wherein the majority of the anthocyanins are pelargonidin-based anthocyanins having a high acylation degree (i.e. molar ratio of acylated anthocyanins to all anthocyanins present) and having a specific minimum degree of acylation by hydroxycinnamic acid (i.e. a specific minimum amount of anthocyanins acylated with hydroxycinnamic acid).

Thus, the present invention provides a composition, which is an anthocyanin-based colorant composition comprising 50-90 mol-%, based on the total amount of anthocyanins, of pelargonidin-based anthocyanins, and wherein (i) ≥70 mol-% of all anthocyanins are acylated with at least one organic acid or at least one phenolic acid; and (ii) 20 mol-% of all anthocyanins are acylated with at least one hydroxycinnamic acid;

and wherein the composition has a red color with a hue value H in the L*C*h* color system in the range of 10-30, measured at an L*-value of (70.0±0.1) in a 0.1 mol/l trisodium citrate dihydrate buffer at pH 3 in a 1 cm-length quartz cell using Spectraflash 650 (Datacolor) in transmission mode under D65 illuminant 10 Deg.

Preferably, in the above (i) 70 mol-% of all anthocyanins are acylated with at least one phenolic acid.

Furthermore, the present invention provides the use of the above composition as a food colorant, specifically as a food colorant for beverages, food preparations, dairy, ice cream and confectionary, and preferably for beverages or fruit preparations having a pH in the ranges defined above.

Preferred embodiments of the present invention are outlined in the following description and/or identified in the appended dependent claims.

DETAILED DISCLOSURE OF THE INVENTION

Preferably, the present composition does not have an unpleasant taste and/or odor, and especially no unpleasant taste and/or odor linked to the presence of sulfur compounds. This renders the composition suitable for even coloring foods having a very weak taste and/or odor by themselves, such as pure or slightly flavored mineral waters, milk and various ice creams.

It is known to the skilled person that unpleasant taste and/or odor of foods often is the consequence of the presence of sulfur-containing compounds. This also applies for red radish and red cabbage, wherein sulfur-containing compounds are at least partially responsible for the strong taste and/or odor, and give a very distinct taste and smell to colorant extracts obtained from these vegetables.

In view of the foregoing, it is also preferred that the present composition does not contain sulfur-containing compounds providing an unpleasant taste and/or odor in an amount which makes the taste or odor of the composition unsuitable for food coloring. Preferably, the present composition contains no, or only trace amounts, of such sulfur-containing compounds.

Thus, the present composition preferably fulfils at least one of the following conditions (i)-(iii), more preferably two (I.e. (i)+(ii), (i)+(iii) or (ii)+(iii)), and most preferably all three thereof:

(i) the present composition has no unpleasant taste and/or odor,
(ii) the present composition does not contain a component derived from red radish or red cabbage or, if present, this component as such fulfills the present requirements (i) and/or (iii),
(iii) the present composition contains no or only trace amounts of sulfur-containing compounds.

Especially, the present composition preferably fulfills the conditions (i) and/or (iii), and more preferably does not contain a component derived from red radish or red cabbage.

Anthocyanins (unsubstituted and shown in the cationic form) are compounds of the following chemical formula, wherein the groups $R^{3'}$, $R^{4'}$, $R^3$, $R^5$, $R^6$ and $R^7$ are H, OH or —$OCH_3$:

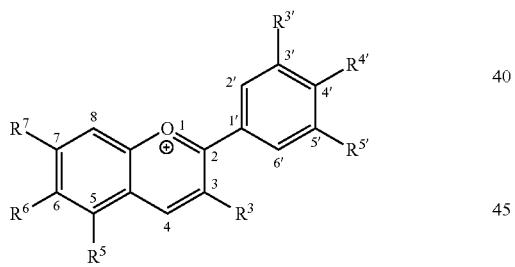

The un-glycosylated forms of anthocyanins are the so-called anthocyanidins. The major representatives among them are cyanidin, delphinidin, malvidin, pelargonidin, peonidin and petunidin, which have the following formulae:

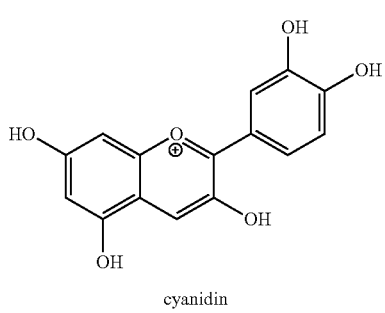

cyanidin

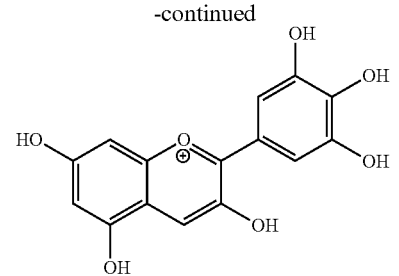

delphinidin

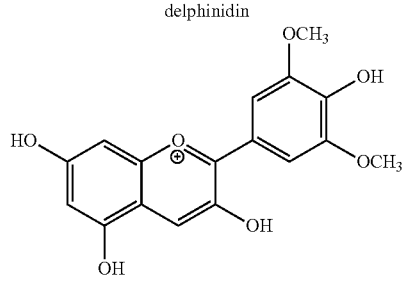

malvidin

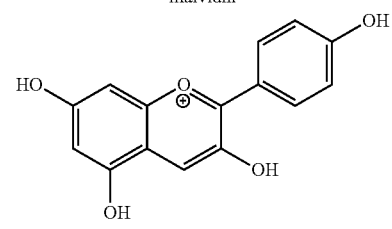

pelargonidin

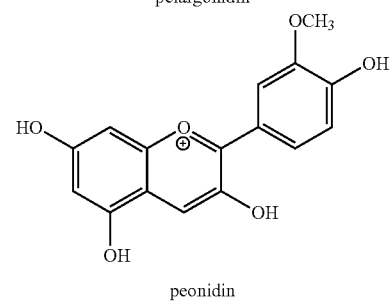

peonidin

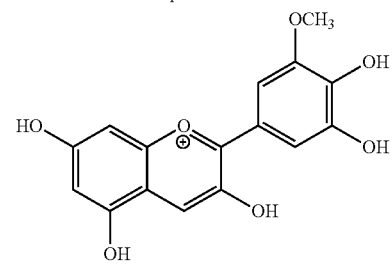

petunidin

Natural anthocyanins in fruit, vegetables and flowers are not present in their aglycone form, but rather are present in form of anthocyanins glycosides. Therein, sugar molecules are bound via an O-glycosidic bond to a hydroxy group, usually present in the 3- and/or 5-position of the anthocyanin molecule. Most commonly, a glycosylation is present on the 3-position and, if present, a second glycosylation is present on the 5-position. However, also a hydroxy group present at position 7, 3', 4' or 5' can be subject to glycosilation. Examples of sugars commonly found in anthocyanin glycosides are glucose, galactose, arabinose, rhamnose and xylose. They can be present as single sugar molecules or in form of di- or tri-saccharides. A glycoside structure can be present in only the 3- or the 5-position of the anthocyanin molecule (monoglycoside) or can be present in both the 3- and the 5-positions thereof (diglycoside). As said above, glycosylations may also be present at other positions.

Further to the substitution by sugar molecules natural anthocyanins can be acylated within the sugar residue structures. Thus, an acylated anthocyanin is an anthocyanin where the hydroxyl group of a sugar residue is substituted by a carboxylic acid under formation of an ester structure, wherein the carboxylic acid is esterified with a sugar moiety. Carboxylic acids suitable for acylation of anthocyanins and frequently found in natural anthocyanins are the hydroxycinnamic acids, (such as coumaric acid, caffeic acid and ferulic acid) and malic acid (see also below).

Phenolic acids are suitable for acylation of anthocyanins. Phenolic acids are carboxylic acids having a phenol ring and a carboxylic acid group and include the groups of the benzoic acids and the already mentioned hydroxycinnamic acids.

In more detail, among the benzoic acid derivatives especially suitable are the so-called hydroxybenzoic acids of the following formula

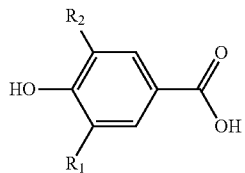

wherein $R_1$ and $R_2$ are each individually H, OH or $OCH_3$, such as p-hydroxybenzoic acid ($R_1=R_2=H$) protocathechuic acid ($R_1=OH$, $R_2=H$), vanillic acid ($R_1=OCH_3$, $R_2=H$), gallic acid ($R_1=R_2=OH$) and syringic acid ($R_1=R$, $=OCH_3$).

Hydroxycinnamic acids generally are understood as a group of compounds of the formula

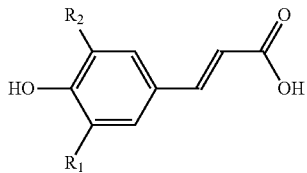

wherein $R_1$ and $R_2$ are each individually H, OH or $OCH_3$, such as p-coumaric acid ($R_1=R_2=H$), caffeic acid ($R_1=OH$, $R_2=H$), ferulic acid ($R_1=OCH_3$, $R_2=H$) and sinapic acid ($R_1=R_2=OCH_3$).

It is known that acylated anthocyanins in general show a higher stability (thermo-stability, photo-stability and chemical stability in physiological and/or food environments) as compared with non-acylated anthocyanins (C. Malien-Aubert et al., *J. Agric. Food Chem.*, 49, 170-176 (2001)). Thus, the presently required degree of acylation (i.e. the amount of acylated anthocyanins) of at least 70 mol-% of all anthocyanins present in the composition of the claimed colorants provides for a sufficient stability of the claimed colorants. Preferably, at least 70 mol-% of all anthocyanins are acylated with at least one phenolic acid. Also preferably, the amount of acylated anthocyanins is at least 80 mol-%, more preferably at least 85 mol-%, even more preferably at least 90 mol-% based on all anthocyanins present in the composition.

As the present inventors have found out, for the provision of highly stable and bright red-orange anthocyanin composition the acylation with hydroxycinnamic acids is especially preferred, i.e. the acylation with hydroxycinnamic acids renders the anthocyanins especially stable against the influences of light, heat and chemical degradation in a food environment. Thus, the degree of acylation by hydroxycinnamic acids in the present compositions is at least 20 mol-%. Although the degree of acylation by hydroxycinnamic acids with respect to stability can be up to 100%, for practical reasons it is preferably 20-80 mol-%, more preferably 25-75 mol-% or even 30-70 mol-% and 35-70 mol-% being especially preferred.

The present invention relates to compositions comprising pelargonidin-based anthocyanins as the major anthocyanin component. More precisely, the amount of pelargonidin-based anthocyanins, based on all anthocyanins present in the composition of the present invention is 50-90 mol-%. Preferably, the amount of pelargonidin-based anthocyanins is 55-85 mol-%, more preferred 60-80 mol-%.

The remainder of other (non-pelargonidin-based) anthocyanin colorants present in the composition of the invention can be any anthocyanin(s) as long as the total amount of anthocyanins shows the amount of acylated anthocyanins and the content of hydroxycinnamic acid acylation moieties defined above, and further shows a red-orange color hue within the range of 10-30, preferably 15-25, measured as defined above.

The other anthocyanins usually represent minor and trace components of anthocyanin extracts obtained from suitable plant stock materials. These other anthocyanins are in general neither necessary nor desired, and can be removed by techniques well known to the person skilled in the art (e.g. by continuous or non-continuous chromatographic processes) However, if desired, other anthocyanins can be intentionally added to a pelargonidin-based anthocyanin composition to obtain a composition according to the invention. Thus, the present composition can be a juice or extract as obtained from a suitable plant stock, or can be further purified and/or supplemented with additional anthocyanin material. Of course, the invention also encompasses mixtures of two or more of any of such anthocyanin compositions.

Also, the present invention encompasses embodiments wherein the anthocyanin component consists of pelargonidin-based anthocyanins.

Also, other (non-anthocyanin) coloring components may be present in the composition of the invention, as long as the color requirements defined herein are met. These can be coloring substances co-existing with anthocyanins in the plant juices or extracts used for preparing the present composition or can be intentionally added colorants of plant or other, preferably natural, origin. However, also these other coloring components are in principle neither necessary nor desired, and thus preferably are kept at low levels.

In another preferred embodiment the present composition contains no non-anthocyanin coloring compounds, i.e. compositions wherein the coloring components consist of anthocyanin compounds are also preferred.

Kuromanin is cyanidin-3-glucoside and is used as a standard for the determination of anthocyanin contents. To this end, a HPLC calibration curve of this compound is made to correlate the HPLC peak area to the kuromanin concentration (in mg/ml). Subsequently, a sample to be investigated is injected in HPLC to obtain a chromatogram, and the peaks areas of the anthocyanin peaks area are integrated and converted into concentrations (in mg/ml) using the kuromanin calibration curve. Thus the concentrations of anthocyanin compounds in the sample are expressed as mg/ml of kuromanin equivalent.

Preferably, the amount of anthocyanin in the composition (kuromanin equivalents), is 2-40 mg/mL, preferably 2-30 mg/ml, more preferably 5-25 mg/ml and especially preferred 8-21 mg/ml or 10-18 mg/ml, for a colorant at 40-60% of dry matter.

However, the present composition can also be present in form of a concentrate. In such a concentrate the dry matter content is preferably 10-95 wt.-%, more preferably 15-85 wt.-% and especially 20-60 wt.-%. Alternatively, the present composition could be present as a powder. In such concentrate or dry powder compositions the anthocyanin content can be preferably be in the range of 1-10 wt.-%, more preferably 2-5 wt.-%, based on the total weight of the composition.

The dry matter content of a sample can be determined by weighing accurately 1-2 g of the sample in liquid or powdered form and putting it into a dry porcelain cupel, storing the cupel in a dry oven at 110° C. for 2 h (powders) or 3 h (liquids), cooling the sample in a desiccator and weighing it again. The dry matter content (wt.-%) is 100×(sample weight after drying/sample weight weighed into the cupel).

Preferably, the present composition is present in the form of a concentrate presenting a ° Brix of 20-80, preferably 25-75 and especially preferred 30-70.

Also, in cases where a plant extract contains the anthocyanins, acylated anthocyanins and/or anthocyanins acylated by hydroxycinnamic acid in insufficient amounts, the respective ranges of the invention as defined above could be achieved by selectively removing undesirable anthocyanin components. This can be achieved by commonly known techniques, such as chromatographic methods as well known to the skilled person in the present technical field. Additionally or alternatively, the missing (depleted) compounds can be added in the amounts needed.

It is to be noted that the sugars for forming anthocyanin glycosides as well as the carboxylic acids forming acylated anthocyanins as mentioned above represent examples and preferred examples only, while the present invention is not restricted to these sugars and/or carboxylic acids.

The present coloring composition has a red-orange color hue having a hue value range in the CIELAB L*C*h* color system in the range of 15-25, when measured at an L* value of (70.0±0.1) in a 0.1 mol/L trisodium citrate dihydrate buffer at pH 3 in a 1 cm length quartz cell using spectra flash 650 (data color, in transmission mode under D65 illuminant 10 Deg).

It is noted that this color range is known to be achievable with extracts from red radish. However, as discussed in detail above, red radish anthocyanin extracts usually show a distinct off taste resulting from the presence of sulfur-containing compounds in red radish, so that these colorant extracts are usually not suitable as food colorants in any application, and especially for coloring beverages and certain foods such as ice cream, dairy and confectionary.

For this reason, and in a specific embodiment, compositions obtained from extracts of red radish are excluded from the present invention.

Also, it should be mentioned that extracts from red radish does not contain detectable amounts of peonidin-based anthocyanins. Thus, in a preferred embodiment 4-15 mol-% of all anthocyanins of the composition are peonidin-based anthocyanins.

The acylation of anthocyanins by at least one organic acid or at least one phenolic acid (preferably by at least one phenolic acid) as well as the specific acylation by hydroxycinnamic acid as required by the present invention can be present in pelargonidin based anthocyanins as well as on other anthocyanins present in addition to the 50-90 mol-% of pelargonidin-based anthocyanins. However, preferably the acylations are predominantly present on the pelargonidin based anthocyanins, and preferably at least 80 mol-%, more preferably at least 85 mol-% of all pelargonidin-based anthocyanins present in the composition are acylated. As upper limit, 100% is possible and included within the scope of the present invention. However, for practical reasons other alternative upper limits are 99 mol-%, 97 mol-% or 95 mol-%.

Even further, also the acylation with hydroxycinnamic acid is predominantly present on pelargonidin-based anthocyanins, and preferably 15-95 mol-% or 25-90 mol-% of the pelargonidin-based anthocyanins present in the present composition are acylated by at least one hydroxycinnamic acid.

Especially preferably, the pelargonidin-based anthocyanins in the present composition include one or both of the following pelargonidin derivatives (1) and (2):

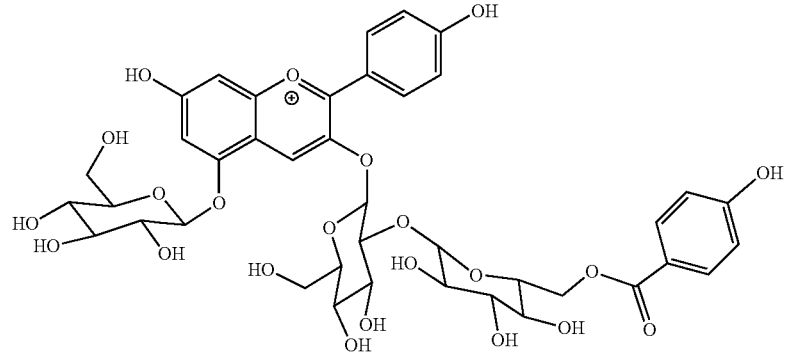

(1)

-continued

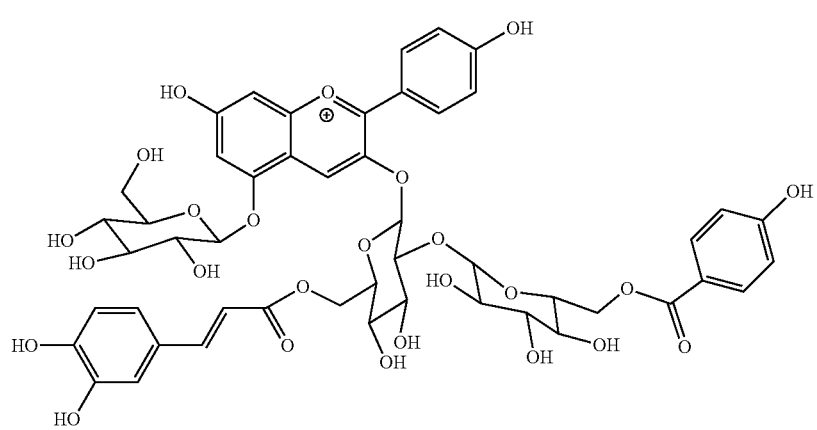

(2)

According to a preferred embodiment of the present invention, the amount of the pelargonidin derivative (1), based on the total amount of anthocyanins present in the composition, is 5-55 mol-%, more preferably 10-50 mol-%, even more preferably 15-45 mol-%, yet more preferably 20-40 mol-% and especially preferably 25-35 mol-%.

Similarly, the content of pelargonidin derivative (2), based on the total amount of anthocyanins present in the composition, is preferably 3-60 mol-%, more preferably 5-58 mol-%, even more preferably 8-56 mol-%, yet more preferably 13-54 mol-% and especially preferably 18-52 mol-% or 23-50 mol-%.

In the foregoing definitions the higher values of the lower limits are more preferred for the reason that the coloring compositions having improved colorant properties are achieved. The lower values of the upper limits are not specifically preferable over higher upper limits in terms of coloring properties, but rather are more easily to achieve in practice from natural plants extracts, and thus may be preferred for commercial reasons.

As already mentioned, the present colorant composition provides a stable and bright red-orange coloring composition, which is especially suited for food coloring, and especially for coloring beverages, food preparations, dairy, ice cream and confectionary. Due to the lack of off taste and off flavors, e.g. off taste and off flavors linked to the presence of sulfur compounds, the present coloring composition can also be used for coloring sensitive food compositions such as beverages, dairy, ice cream and confectionary without negative effect on the overall flavor and taste thereof.

The present composition can, in principle, be made from pure anthocyanin compounds, can be composed from extracts of different plant varieties, or can be obtained by extracting one single plant variety and if needed, refining to obtained extract. Of course, a preferred source of the present composition would be a plant variety the extract of which can directly be used as a composition of the present invention.

Examples of suitable sources are aronia, bilberry, black carrot, blackcurrant, blueberry, cherry, elderberry, hibiscus, lingonberry, purple corn, red grape, red cabbage, purple sweet potato and red sweet potato, and a preferred example is the red variety of sweet potato *Ipomoea batatas* (L.) Lam (referred to hereinafter as RSWP). Thus, preferably the present composition is obtainable from juices or extracts of RSWP, including both compositions consisting of or mainly comprising juices or extracts of RSWP.

In the following the present invention will be described by examples and comparative examples without being limited thereto.

EXAMPLES

As an illustrative example of a colorant of the invention and a procedure for its preparation the extraction and characterization of anthocyanins from Red Sweet Potato (RSWP), i.e. the red variety of *Ipomoea batatas* (L.) Lam, will be described.

As a reference, carminic acid has been used in some instances herein, since it obtains a very stable orange shade when it is added to beverages and thus can be seen as a reference colorant in at least this field of application. However, the legally admissible concentrations of carminic acid in beverages are too low to achieve the color shades as achievable with anthocyanins, and especially as achievable with the composition of the present invention. Thus, while a comparison with carminic acid at the intended color shades might show a superior stability of carminic acid, such an embodiment would be unsuitable in practice due to inadmissible high carminic acid levels. Therefore, carminic acid has been used as a reference only, for comparison known anthocyanins have been chosen.

Example 1

Characterization of Major Anthocyanins from RSWP
A) Extraction

A RSWP concentrate prepared by chopping RSWP tubers into slices and "washing" them 4 times with acidified water to conduct an extraction, and then subjecting the obtained extract to micro-filtration and subsequent purified on an absorbing resin. The resulting anthocyanin extract was concentrated and then pasteurized.

Anthocyanins were isolated and concentrated on a Sep-Pak C18 cartridge (Waters®)®) The cartridge was washed with 2 ml of methanol and then with 2 ml of acidified water (HCl 0.3%) before loading few drops of RSWP concentrate. Once the cartridge has been washed with 4 ml of acidified water (HCl 0.3%), and then with 2 ml of ethyl acetate, anthocyanins were finally eluted with a minimum volume of acidified methanol (HCl 0.1%).

B) Analysis

The anthocyanin extract was analyzed by fast-HPLC/ESI-TI. Separation was obtained at 30° C. using a BEH (Waters®) C18 Column (50 mm×2.1 mm, 1.8 μm), by injecting 1 μL of the filtered extract. The mobile phase consisted of two solvents: A, Water/Acetonitrile/HCOOH (95.7/3.3/1, v/v/v) and B, Water/Acetonitrile/HCOOH (44/55/1, v/v/v) at a flow rate of 0.8 ml/min. The gradient used was as follows:

| Time in min | Solvent A (vol.-%) | Solvent B (vol.-%) |
|---|---|---|
| 0 | 94 | 6 |
| 3.3 | 80 | 20 |
| 6 | 60 | 40 |
| 7 | 40 | 60 |
| 8 | 94 | 6 |
| 11 | 94 | 6 |

Mass spectrometry analyses were performed on a Bruker Daltonics HCT Ultra, operating in the positive electrospray ionization mode. Ions to be fragmented in $MS^2$ or $MS^3$ were automatically chosen by the software. Fragmentation is obtained through a screening of power leading in a determination of the minimal power necessary to break down the linkages.

C) Results and Discussion

Figure 1:
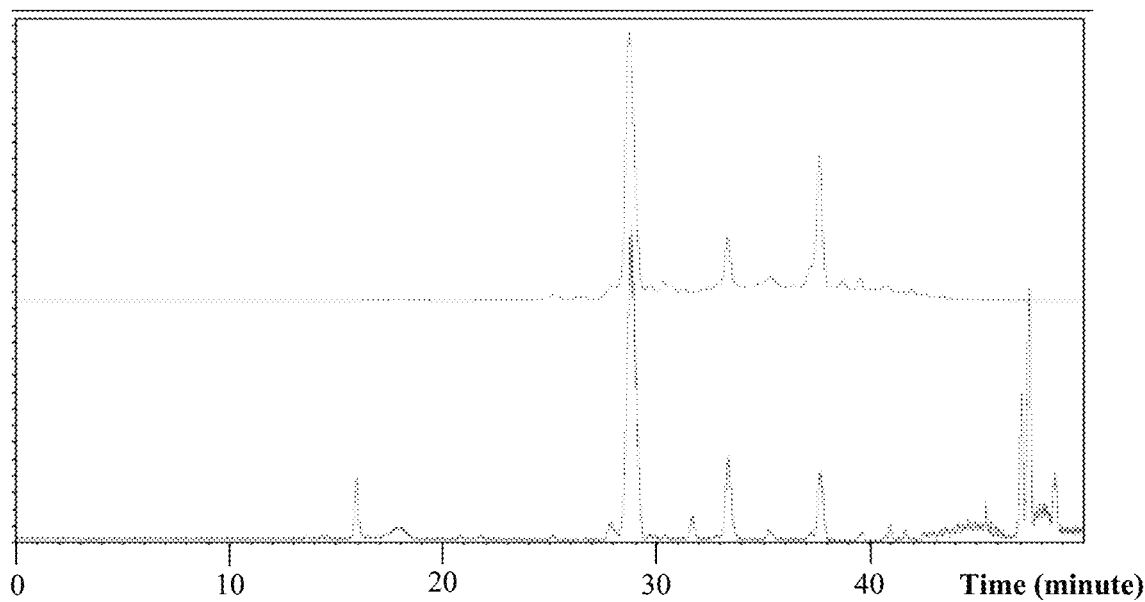
FIG. 1 Chromatographic profile (top) at 520 nm and mass fingerprint (bottom) of anthocyanins from red sweet potato.
Figure 2:
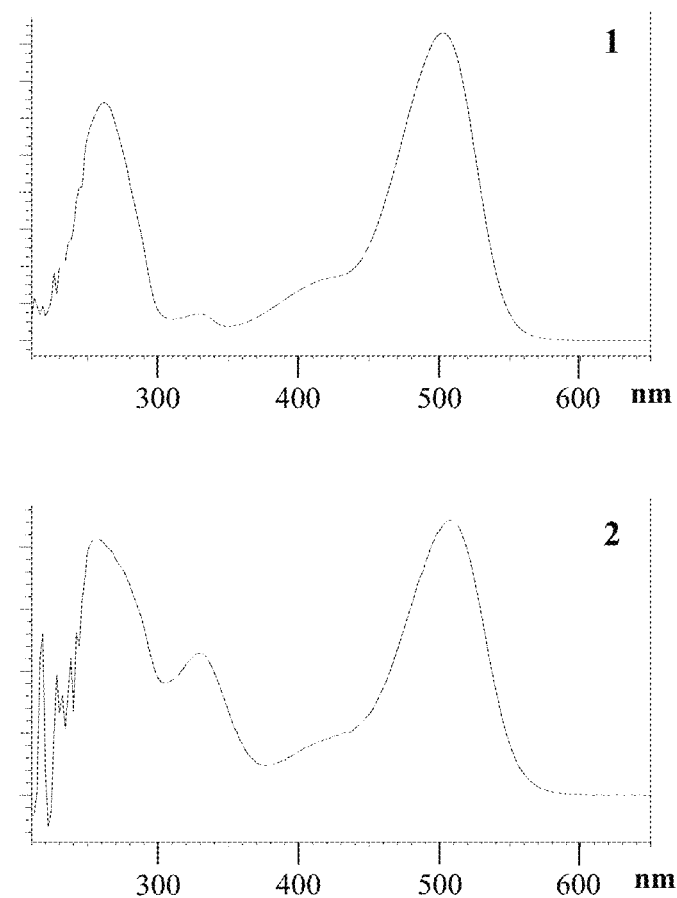
FIG. 2 UV-visible spectra of the two major anthocyanins isolated from red sweet potato extract.
Figure 3:
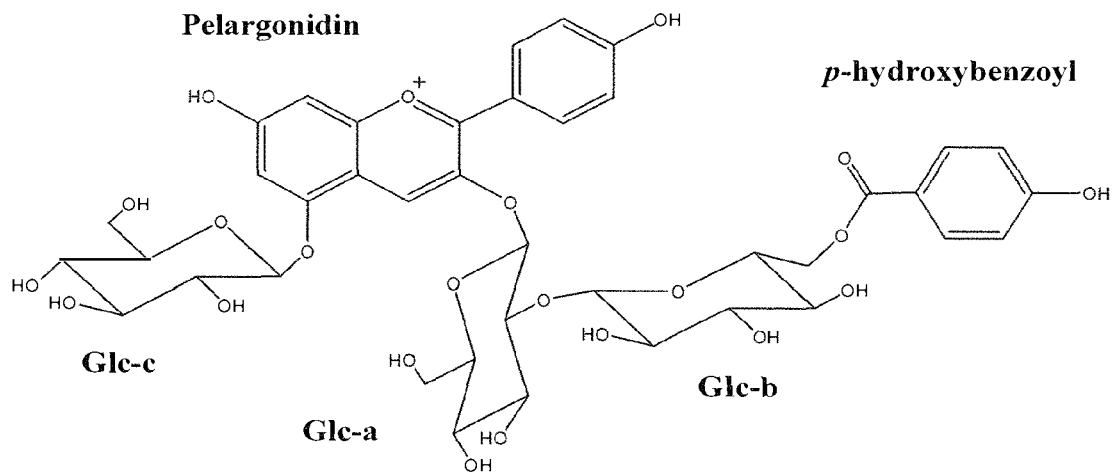
FIG. 3 Structure of Anthocyanin 1.
Figure 4:
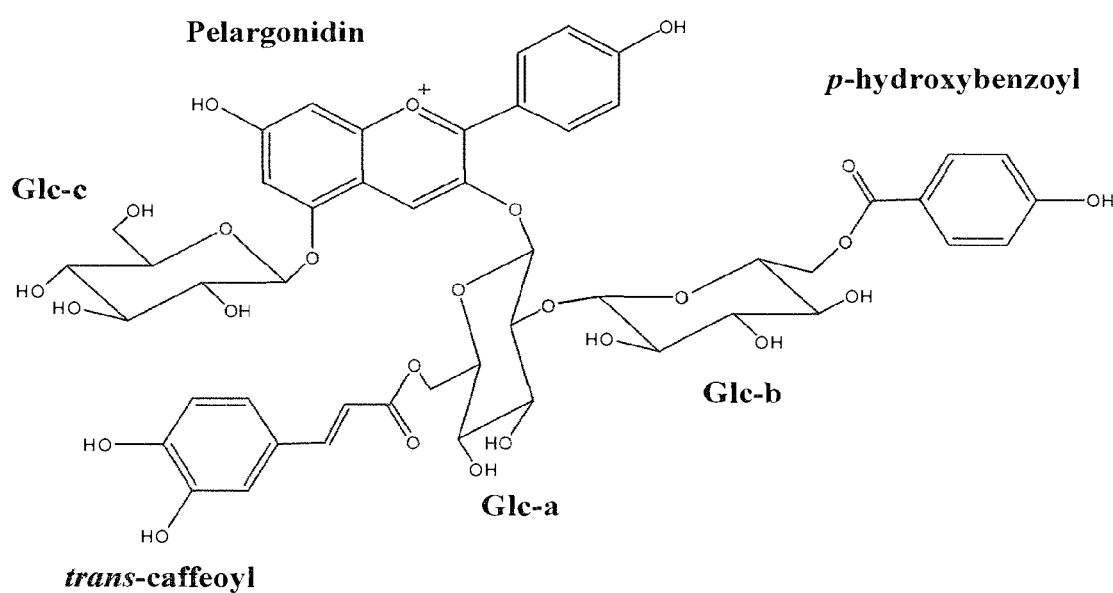
FIG. 4 Structure of Anthocyanin 2.

The chromatographic profile of anthocyanins from RSWP is presented on FIG. 1. This profile reflects the presence of two major peaks, eluted at 28.8 and 37.6 min, and numerous other anthocyanins in low amount. Thanks to mass spectrometry data, eleven different compounds were characterized; their maximum absorption wavelength and their mass fragmentations are displayed in Table 1. A tentative identification of the core anthocyanin of each compound was realized, and shows a majority of pelargonidin-derived pigments in RSWP.

Mass spectrometry revealed the presence of two different anthocyanins under the major peak, this peak being principally made up of the compound based on pelargonidin (m/z 877).

This first characterization of anthocyanin from RSWP showed the presence of two major anthocyanins referred to herein as Anthocyanin 1 and Anthocyanin 2, respectively. These compounds have molecular weight of 877 and 1039 g/mol and are both based on pelargonidin. Their characteristics are shown in Table 1, together with other pelargonidin-based anthocyanins found in minor amounts in RSWP.

TABLE 1

| Rt (min) | $\lambda_{MAX}$ (nm) | m/z $[M + H]^+$ | Fragment ions (m/z) | Associated pelargonidin |
|---|---|---|---|---|
| 28.8 | 504 | 877 | 715, 433, 271 | Anthocyanin 1 |
| 33.4 | 504 | 933 | 771, 433, 271 | other |
| 35.3 | 526 | 919 | 757, 433, 271 | other |
| 37.6 | 508 | 1039 | 877, 433, 271 | Anthocyanin 2 |
| 39.6 | 508 | 1095 | 933, 271 | other |

Based on the areas of peaks visible on FIG. 1 the content of pelargonidin-based anthocyanins present in the extract was found to be about 58 mol-%. The amount of Anthocyanin 1 and Anthocyanin 2, based on all anthocyanins, was estimated to be 46.1 mol-%.

Example 2

Extraction and Isolation of the Major Anthocyanins

A RSWP concentrated extract at 8 CU/kg was extracted using ethyl acetate in order to remove phenolic compounds except anthocyanins. A volume of 30 ml of concentrated extract was diluted in 270 ml of acidified water (pH3) and then washed three times with 300 ml of ethyl acetate. The aqueous phase was concentrated under vacuo.

The anthocyanin extract obtained was purified on a Sephadex LH20 column (400 mm×260 mm, Pharmacia), being eluted with acetic acid/water (4.6:100, v/v) at a flow rate of 16 ml/h. Two red-colored bands were collected. All fractions collected were analyzed by HPLC and fractions of high purity 85% were grouped together.

Analytical HPLC was performed using a LiChrosorb RP-18 Column (250 mm×4.6 mm, 5.0 μm) by injecting 10 μl of the filtered extracts. A combination of two solvents was used for elution: A, Water/HCOOH/Acetonitrile (87/10/3, v/v/v) and B, Water/HCOOH/Acetonitrile (40/10/50, v/v/v). The column flow was set at 0.8 ml/min. and the column temperature at 30° C. The gradient used was as summarized below:

| Time (min) | Solvent A (vol.-%) | Solvent B (vol.-%) |
|---|---|---|
| 0 | 94 | 6 |
| 20 | 80 | 20 |
| 35 | 60 | 40 |
| 40 | 40 | 60 |
| 45 | 10 | 90 |
| 50 | 10 | 90 |

Fractions containing high purity of one of the two anthocyanins of interest were grouped together and then concentrated under vacuo before freeze-drying. Powders of each anthocyanin were analyzed by NMR.

Example 3

NMR Analyses
A) Methods

The NMR experiments (¹H, COSY, ROESY, HSQC, HSQC-TOCSY, HMBC, ¹³C) were obtained at 600.13 MHz on a BRUKER Avance II 600 instrument equipped with a TCI ¹H—¹³C/¹⁵N CryoProbe at 27° C. Dried samples were solubilized in 500 μl in DMSO-d6-TFA-d 99.99% 90:10.

B) Results and Discussion

Anthocyanins 1 and 2 were isolated in sufficient amounts to be characterized by NMR. Their structures were identified by ¹H and ¹³C NMR spectroscopy in DMSO/TFA (90:10). Tables 2 and 3 show the ¹H and ¹³C assignment and HSQC and TOCSY correlations of Anthocyanin 1 and Anthocyanin 2, respectively. Therein un=unresolved, s=singlet, d=doublet and t=triplet.

TABLE 2

| ATOM | $\delta_{13C}{}^a$ | $\delta_{1H}{}^b$ | Correlations |
|---|---|---|---|
| Pelargonidin | | | |
| 1 | — | — | |
| 2 | 162.7 | — | |
| 3 | 144.3 | — | |
| 4 | 135.3 | 8.94; s | ROESY (Glc-a-1) |
| 5 | 155.4 | — | |
| 6 | 104.3 | 6.97; d (1.5) | ROESY (Glc-c-1) |
| 7 | 168.1 | — | |
| 8 | 96.4 | 7.09; d (1.5) | |
| 9 | 155.7 | — | |
| 10 | 111.9 | — | |
| 1' | 119.3 | — | |
| 2' | 135.3 | 8.58; d (8.8) | |
| 3' | 117.1 | 7.07; d (8.8) | |
| 4' | 165.4 | — | |
| 5' | 117.1 | 7.07; d (8.8) | |
| 6' | 135.3 | 8.58; d (8.8) | |
| Glucose-a | | HSQC-TOCSY (100.1; 80.3; 77.6; 76.5; 69.5; 60.7) | |
| 1 | 100.1 | 5.46; d (7.7) | HMBC (Pelar-3), ROESY (Glc-a-2, 3, 5, Pelar-4) |
| 2 | 80.3 | 3.92; t (8.4) | HMBC (Glc-a-1, 3, Glc-b-1), ROESY (Glc-b-1) |
| 3 | 76.5 | 3.63; t (9.0) | |
| 4 | 69.5 | 3.30; t (8.8) | |
| 5 | 77.6 | 3.49; un | |
| 6 | 60.7 | 3.69; d (10) 3.46; un | |
| Glucose-b | | HSQC-TOCSY (104.0; 76.5; 74.6; 74.3; 69.8; 63.2) | |
| 1 | 104.0 | 4.84; d (7.7) | HMBC (Glc-3), ROESY (Glc-a-2, Glc-b-2, 3, 5) |
| 2 | 74.6 | 3.08; t (8.8) | |
| 3 | 76.5 | 3.24; t (8.8) | |
| 4 | 69.8 | 3.27; un | |
| 5 | 74.3 | 3.23; un | |
| 6 | 63.2 | 4.14; dd (12.5; 2.2) 4.09; dd (11.7; 4.8) | |
| Glucose-c | | HSQC-TOCSY (101.4; 77.6; 76.0; 73.2; 69.7; 60.7) | |
| 1 | 101.4 | 5.12; d (7.7) | HMBC (Pelar-5), ROESY (Glc-c-2, 3, 5, Pelar-6) |
| 2 | 77.6 | 3.46; un | |
| 3 | 76.0 | 3.36; t (9.2) | |
| 4 | 69.7 | 3.27; un | |
| 5 | 77.6 | 3.46; un | |
| 6 | 60.7 | 3.74; dd (13.3; 2.2) 3.54; dd (11.9; 5.3) | |
| p-hydroxybenzoate | | | |
| 1 | 165.5 | — | |
| 2 | 120.3 | — | |
| 3 | 131.5 | 7.56; d (8.8) | |
| 4 | 115.3 | 6.67; d (8.8) | |
| 5 | 161.9 | — | |
| 6 | 115.3 | 6.67; d (8.8) | |
| 7 | 131.5 | 7.56; d (8.8) | |
| Pelargonidin | | | |
| 1 | — | — | |
| 2 | 162.7 | — | |
| 3 | 144.3 | — | |
| 4 | 135.3 | 8.94; s | ROESY (Glc-a-1) |
| 5 | 155.4 | — | |
| 6 | 104.3 | 6.97; d (1.5) | ROESY (Glc-c-1) |
| 7 | 168.1 | — | |

TABLE 2-continued

Anthocyanin 1

| ATOM | $\delta_{13C}{}^a$ | $\delta_{1H}{}^b$ | Correlations |
|---|---|---|---|
| 8 | 96.4 | 7.09; d (1.5) | |
| 9 | 155.7 | — | |
| 10 | 111.9 | — | |
| 1' | 119.3 | — | |
| 2' | 135.3 | 8.58; d (8.8) | |
| 3' | 117.1 | 7.07; d (8.8) | |
| 4' | 165.4 | — | |
| 5' | 117.1 | 7.07; d (8.8) | |
| 6' | 135.3 | 8.58; d (8.8) | |
| Glucose-a | | HSQC-TOCSY (100.1; 80.3; 77.6; 76.5; 69.5; 60.7) | |
| 1 | 100.1 | 5.46; d (7.7) | HMBC (Pelar-3), ROESY (Glc-a-2, 3, 5, Pelar-4) |
| 2 | 80.3 | 3.92; t (8.4) | HMBC (Glc-a-1, 3, Glc-b-1), ROESY (Glc-b-1) |
| 3 | 76.5 | 3.63; t (9.0) | |
| 4 | 69.5 | 3.30; t (8.8) | |
| 5 | 77.6 | 3.49; un | |
| 6 | 60.7 | 3.69; d (10) | |
| | | 3.46; un | |
| Glucose-b | | HSQC-TOCSY (104.0; 76.5; 74.6; 74.3; 69.8; 63.2) | |
| 1 | 104.0 | 4.84; d (7.7) | HMBC (Glc-3), ROESY (Glc-a-2, Glc-b-2, 3, 5) |
| 2 | 74.6 | 3.08; t (8.8) | |
| 3 | 76.5 | 3.24; t (8.8) | |
| 4 | 69.8 | 3.27; un | |
| 5 | 74.3 | 3.23; un | |
| 6 | 63.2 | 4.14; dd (12.5; 2.2) | |
| | | 4.09; dd (11.7; 4.8) | |
| Glucose-c | | HSQC-TOCSY (101.4; 77.6; 76.0; 73.2; 69.7; 60.7) | |
| 1 | 101.4 | 5.12; d (7.7) | HMBC (Pelar-5), ROESY (Glc-c-2, 3, 5, Pelar-6) |
| 2 | 77.6 | 3.46; un | |
| 3 | 76.0 | 3.36; t (9.2) | |
| 4 | 69.7 | 3.27; un | |
| 5 | 77.6 | 3.46; un | |
| 6 | 60.7 | 3.74; dd (13.3; 2.2) | |
| | | 3.54; dd (11.9; 5.3) | |
| p-hydroxybenzoate | | | |
| 1 | 165.5 | — | |
| 2 | 120.3 | — | |
| 3 | 131.5 | 7.56; d (8.8) | |
| 4 | 115.3 | 6.67; d (8.8) | |
| 5 | 161.9 | — | |
| 6 | 115.3 | 6.67; d (8.8) | |
| 7 | 131.5 | 7.56; d (8.8) | |

TABLE 3

Anthocyanin 2

| ATOM | $\delta_{13C}{}^a$ | $\delta_{1H}{}^b$ | Correlations |
|---|---|---|---|
| Pelargonidin | | | |
| 1 | — | — | |
| 2 | 163.0 | — | |
| 3 | 144.2 | | |
| 4 | 135.2 | 8.83; s | ROESY (Glc-a-1) |
| 5 | 155.4 | — | |
| 6 | 104.9 | 6.93; d (1.8) | ROESY (Glc-c-1) |
| 7 | 168.3 | — | |
| 8 | 96.1 | 9.97; s | |
| 9 | 155.6 | — | |
| 10 | 112.0 | | |
| 1' | 119.3 | — | |
| 2' | 135.2 | 8.50; d (8.8) | |
| 3' | 117.2 | 7.04; d (8.8) | |
| 4' | 165.5 | — | |
| 5' | 117.2 | 7.04; d (8.8) | |
| 6' | 135.2 | 8.50; d (8.8) | |

TABLE 3-continued

Anthocyanin 2

| ATOM | $\delta_{13C}{}^a$ | $\delta_{1H}{}^b$ | Correlations |
|---|---|---|---|
| Glucose-a | | HSQC-TOCSY (100.3; 81.3; 76.1; 74.3; 69.9; 63.3) | |
| 1 | 100.3 | 5.54; d (7.3) | HMBC (Pelar-3), ROESY (Glc-a-2, 3, 5, Pelar-4) |
| 2 | 81.3 | 3.95; t (8.1) | HMBC (Glc-a-2), ROESY (Glc-a-2, Glc-b-2, 3, 5) |
| 3 | 76.1 | 3.69; t (8.8) | |
| 4 | 69.9 | 3.42; t (9) | |
| 5 | 74.3 | 3.83 | |
| 6 | 63.3 | 4.37; d (12.5) | HMBC (trans-caffeoyl-1), ROESY (Glc-a-4, 5) |
| | | 2.25; dd (11.8; 6.2) | |
| Glucose-b | | HSQC-TOCSY (104.4; 76.4; 74.8; 74.3; 69.9; 63.1) | |
| 1 | 104.4 | 4.78; d (7.7) | HMBC (Glc-a-2), ROESY (Glc-a-2, Glc-b-2, 3, 5) |
| 2 | 74.8 | 3.14; t (8.4) | |
| 3 | 76.4 | 3.25; un | |
| 4 | 69.9 | 3.25; un | |
| 5 | 74.3 | 3.25; un | |
| 6 | 63.1 | 4.11; d (11) | |
| | | 4.06; dd (11.7; 4.0) | |
| Glucose-c | | HSQC-TOCSY (102.0; 77.9; 76.1; 73.4; 69.9; 61.0) | |
| 1 | 102.0 | 5.09; d (8.1) | HMBC (Pelar-5), ROESY (Glc-c-2, 3, 5, Pelar-6) |
| 2 | 73.4 | 3.51; t (8.4) | |
| 3 | 76.1 | 3.36; t (9.9) | |
| 4 | 69.9 | 3.25; un | |
| 5 | 77.9 | 3.48 | |
| 6 | 61.0 | 3.77; d (11.0) | |
| | | 3.54; dd (12.0; 5.9) | |
| p-hydroxybenzoat | | | |
| 1 | 165.5 | — | |
| 2 | 120.5 | — | |
| 3 | 131.5 | 7.49; d (8.8) | |
| 4 | 115.3 | 6.62; d (8.8) | |
| 5 | 162.1 | — | |
| 6 | 115.3 | 6.62; d (8.8) | |
| 7 | 131.5 | 7.49; d (8.8) | |
| trans-caffeoyl | | | |
| 1 | 166.8 | — | |
| 2 | 113.8 | 6.09; d (15.9) | |
| 3 | 145.8 | 7.27; d (15.9) | |
| 4 | 125.6 | — | |
| 5 | 115.4 | 6.91; d (1.5) | |
| 6 | 145.6 | — | |
| 7 | 148.6 | — | |
| 8 | 116.0 | 6.73; d (8.1) | |
| 9 | 121.6 | 6.81; dd (8.4; 1.8) | |

From the above data Anthocyanin 1 was identified as pelargonidin 3-O-(2-O-(6-O-para-hydroxybenzoyl-glucopyranosyl)-glucopyranoside)-5-O-glucopyranoside:

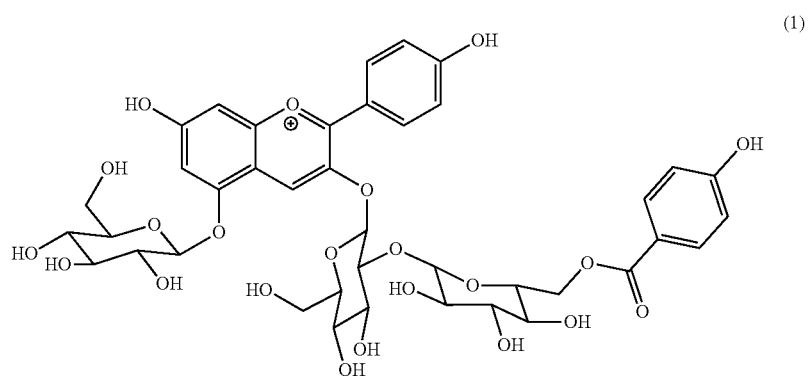 [SMILES: O=C(OCC1OC(OC2C(Oc3cc4c(OC5OC(CO)C(O)C(O)C5O)cc(O)cc4[o+]c3-c3ccc(O)cc3)OC(CO)C(O)C2O)C(O)C(O)C1O)c1ccc(O)cc1]

(1)

Similarly, Anthocyanin 2 has been identified as pelargonidin 3-O-(2-O-(6-O-para-hydroxybenzoyl-glucopyranosyl)-6-O-trans-caffeoyl-glucopyranoside)-5-O-glucopyranoside:

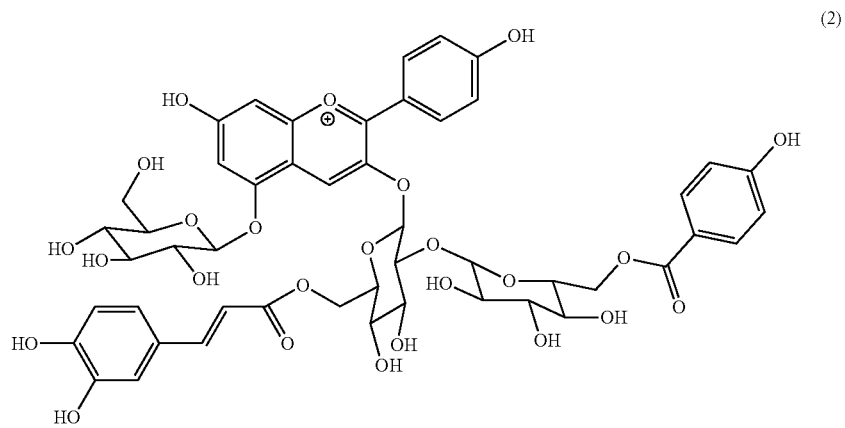 [SMILES: O=C(/C=C/c1ccc(O)c(O)c1)OCC1OC(Oc2cc3c(OC4OC(CO)C(O)C(O)C4O)cc(O)cc3[o+]c2-c2ccc(O)cc2)C(OC2OC(COC(=O)c3ccc(O)cc3)C(O)C(O)C2O)C(O)C1O]

(2)

These structures are in agreement with mass spectrometry data and UV-visible spectra discussed above.

Example 4

Shade and Stability of Liquid Bulk Made from RSWP

RSWP liquid concentrate is evaluated for its shade against other anthocyanin references and for stability during cold storage.

A) Preparation of RSWP Concentrate

Sliced tubers were exhausted through extractions with acidified water. After clarification step, filtrate was purified onto an absorbent resin. Final concentration leads to a product at 65° Brix.

B) Color Evaluation and Stability Test

Shade conferred by RSWP concentrate was evaluated against other anthocyanin reference, the red radish, having similar shade but presenting off-flavors (sulfur compounds).

Samples of liquid concentrate were stored in cold room at 4-8° C. during 6 months including regular analytical evaluation. Samples were sacrificed after each evaluation. Bulk stability was evaluated through spectrophotometric and colorimetric measurements, turbidity, and amount of sludges.

Spectrophotometric measurements were performed in 1 cm-length quartz cell in a pH3 buffer using spectrophotometer HP8354. Red sweet potato concentrate was characterized through color strength $E_3$ (expressed in color unit/kg).

Colorimetric measurements were performed in 1 cm-length quartz cell in a pH3 buffer using Spectraflash 650 (Datacolor) in transmission mode under D65 illuminant 10 Deg. Turbidity was measured on a VWR turbidimeter.

C) Results

Table 4 provides comparative color parameters of RSWP concentrate and red radish powder, and Table 5 shows the cold storage stability of RSWP concentrate.

TABLE 4

|  | L* | C | h |
| --- | --- | --- | --- |
| RSWP concentrate | 70.0 | 62 | 23 |
| Red Radish powder | 70.0 | 63 | 17 |

RSWP concentrate presents similar brightness as pure red radish but its shade is more red-orange.

TABLE 5

|  | $E_3$ (CU/kg) | L* | C | h | Turbidity | Sludges |
| --- | --- | --- | --- | --- | --- | --- |
| t0 | 8.2 ± 0.1 | 70 | 62 | 23 | <1 NTU | <0.1% |
| t0 + 1 mth | 8.6 ± 0.1 | 70 | 61 | 23 | <1 NTU | <0.1% |
| t0 + 2 mths | 8.0 ± 0.1 | 70 | 62 | 24 | <1 NTU | <0.1% |
| t0 + 4 mths | 8.3 ± 0.1 | 70 | 62 | 23 | <1 NTU | <0.1% |
| t0 + 5 mths | 8.3 ± 0.1 | 70 | 61 | 23 | <1 NTU | <0.1% |
| t0 + 6 mths | 8.1 ± 0.1 | 70 | 62 | 23 | <1 NTU | <0.1% |

RSWP concentrate kept in cold conditions is highly stable considering color as well as physico-chemical parameters.

Example 5

Stability in Beverage Application of a Color Made from RSWP

RSWP concentrate is evaluated in a model beverage medium submitted to a pasteurization step for determining cold, heat and light stabilities against two standard references having similar shades and being used in this application.

A) Preparation of Colored Model Beverage Medium

The model beverage medium was prepared according to the following recipe.

| | |
| --- | --- |
| Saccharose | 43.00% |
| Potassium Sorbate | 0.09% |
| Sodium Benzoate | 0.07% |
| Citric acid anhydrous | 0.86% |
| Milli Q water | 55.98% |

A soft drink concentrate around 40° Brix was obtained and further diluted with Milli Q water until 11° Brix. The pH was finally adjusted to 3.0±0.2 with citric acid.

As colorant RSWP concentrate at 0.22% was added directly into the model beverage medium. For comparison a red radish/black carrot anthocyanin blend (referred to as rr/bc hereinafter) at 0.13% and having basically the same color shade was used. As a reference (DE* 2000=0) 8.2 wt.-% carminic acid was used in an amount of 0.4 wt.-% After submission to a pasteurization step (referred to as HT) at 92° C. for 40 seconds, the colored beverages were poured into PET bottles and then stored under the following conditions:

For light stability: daylight exposure, room temperature
For heat stability: in a binder incubator at 40° C., 65% RH
For reference storage: in a cold room at 4° C. in the dark Colorimetric follow-up was done every week during one month and then after 2-month storage. Measurements were performed directly on the PET bottles using Spectraflash 650 (Datacolor) in transmission mode under D65 illuminant 10 Deg.

B) Results

Table 6 summarizes the shades of the model beverage medium colored with RSWP or the references at day 0.

TABLE 6

|  | L* | C | h | DE* 2000 |
|---|---|---|---|---|
| Carminic acid 0.4% | 38.80 | 94.02 | 44.64 |  |
| RSWP concentrate | 39.26 | 92.89 | 45.90 | 1.15 |
| red radish/black carrot (rr/bc) | 39.46 | 90.88 | 45.14 | 0.93 |

*DE* 2000 is an indicator for the total color variation, which includes the changes all of L*, C and h values and illustrates the total color difference. High values indicate large differences.

Beverage colored with RSWP is slightly duller than the one colored with carminic acid but is brighter than the beverage colored with rr/bc. Shades brought by the RSWP concentrate and the comparison (rr/bc) and the reference (carminic acid) are similar.

Table 7 shows the color stability after pasteurization (HT) of the model beverage medium colored with RSWP or rr/bc.

TABLE 7

|  | L* | C | h | DE* 2000 |
|---|---|---|---|---|
| Carminic acid before HT | 38.80 | 94.02 | 44.64 |  |
| Carminic acid after HT | 38.62 | 93.59 | 44.65 | 0.18 |
| RSWP before HT | 39.26 | 92.89 | 45.90 |  |
| RSWP after HT | 39.55 | 93.35 | 46.00 | 0.28 |
| red radish/black carrot before HT | 39.46 | 90.88 | 45.14 |  |
| red radish/black carrot after HT | 40.00 | 90.96 | 45.18 | 0.47 |

Beverage colored with RSWP is more stable through pasteurization compared to the beverage colored with rr/bc. However it remains slightly more sensitive than a beverage colored with carminic acid.

Figure 5:
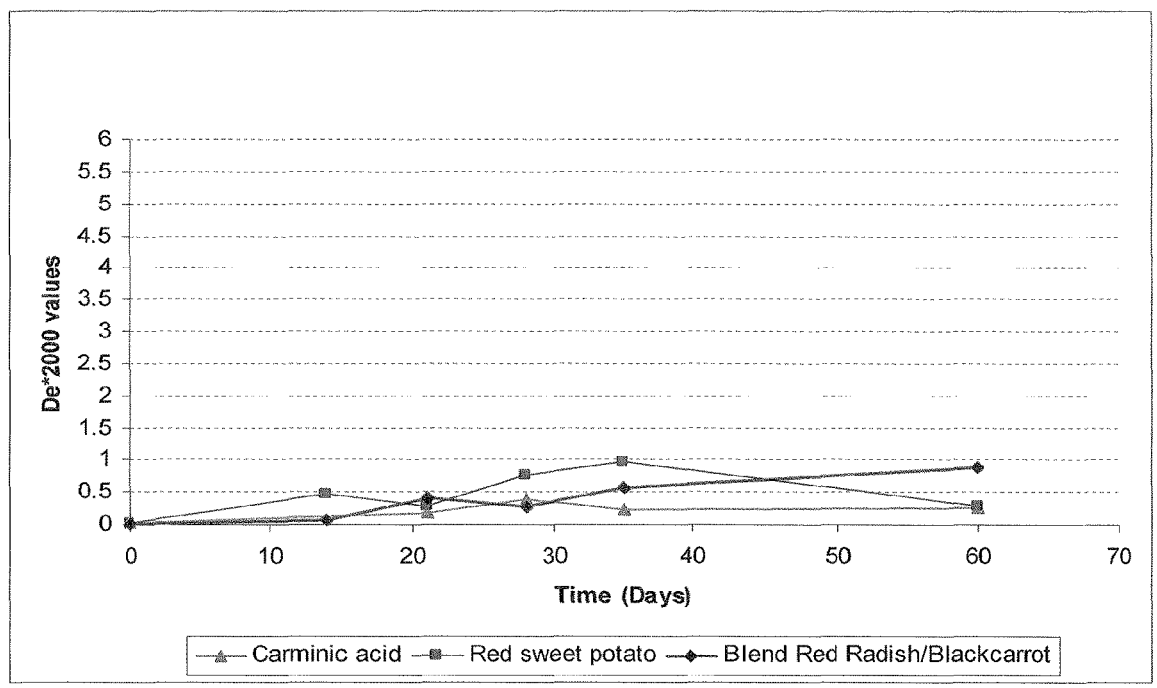
FIG. 5 Evolution of DE* 2000 during the 2-month storage of colored model beverage medium in cold room.

FIG. 5 shows the evolution of DE* 2000 along the 2-month storage of colored model beverage medium in cold room.

Beverages colored with carminic acid, RSWP or rr/bc, respectively, present similar stabilities under cold storage. Evolution of coloration is not visually detected whatever the color reference.

Figure 6:
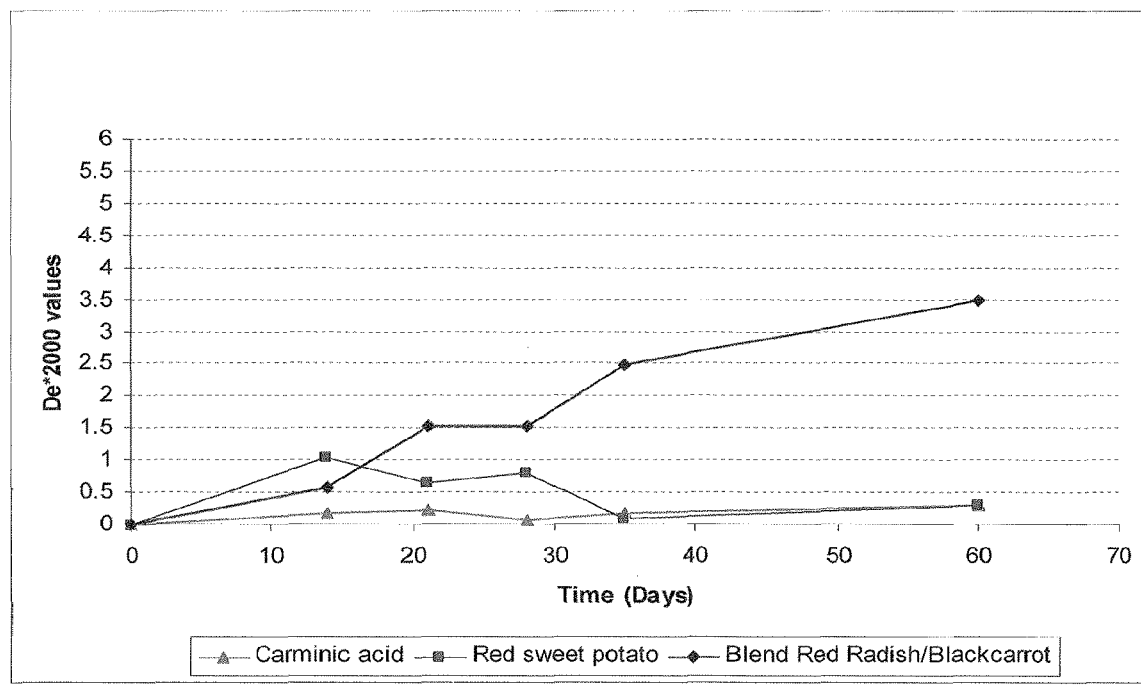
FIG. 6 Evolution of DE* 2000 during the 2-month storage of colored model beverage medium under light exposure.
Figure 7:
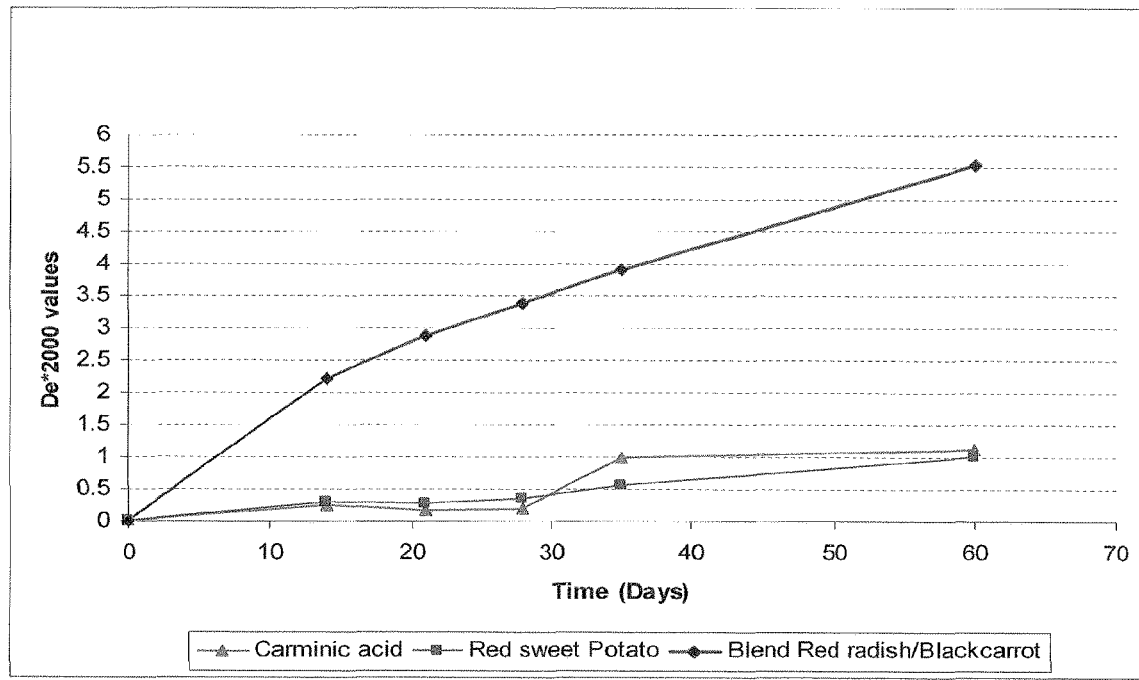
FIG. 7 Evolution of DE* 2000 during the 2-month storage of colored model beverage medium under heat exposure.

The evolution of DE* 2000 during the 2-month storage of colored model beverage medium under (i) light exposure and (ii) heat exposure is shown in FIGS. 6 and 7, respectively.

The beverage colored with RSWP is as stable as the one colored with carminic acid after 2-month light exposure (no visual shift of shade is detected in both cases) and is far more stable in both tests than a beverage colored with rr/bc, which undergoes a wide evolution of coloration.

Example 6

Impact of Ascorbic Acid on the Color Stability of Beverage colored with RSWP extract A) Experimental RSWP concentrate is evaluated in a model beverage medium containing ascorbic acid for determining cold, heat and light stabilities against a standard reference having similar shade.

The model beverage medium prepared in Example 5 was used, except that 250 ppm ascorbic acid was added before final adjustment of pH to 3.0±0.2 with citric acid.

The colors were added in the same manner as described in Example 5, and then the colored beverages were poured into PET bottles and stored under the conditions defined in Example 5. Colorimetric follow-up and measurements were then also performed as defined in Example 5.

B) Results

Figure 8:
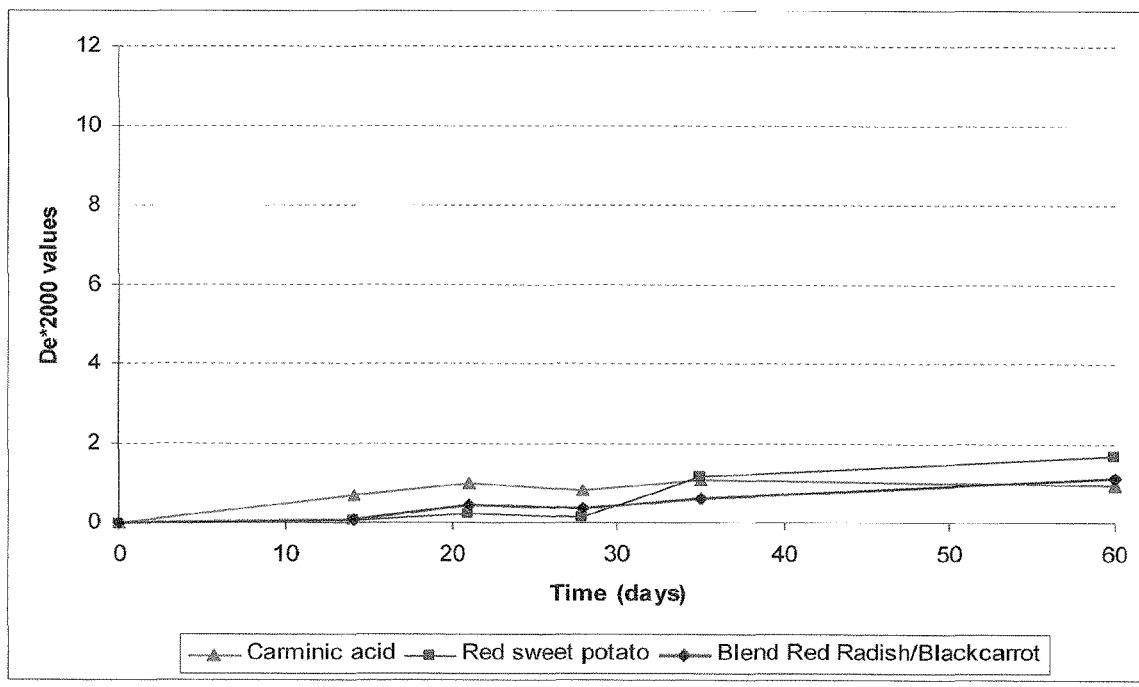
FIG. 8 Evolution of DE* 2000 during the 2-month storage of colored model beverage medium containing ascorbic acid in cold room.

FIG. 8 shows the evolution of DE* 2000 along the 2-month storage of colored model beverage medium in cold room.

Beverages colored with carminic acid, RSWP or rr/bc, respectively, present similar stabilities under cold storage. Evolution of coloration is not visually detected whatever the color reference.

Figure 9:
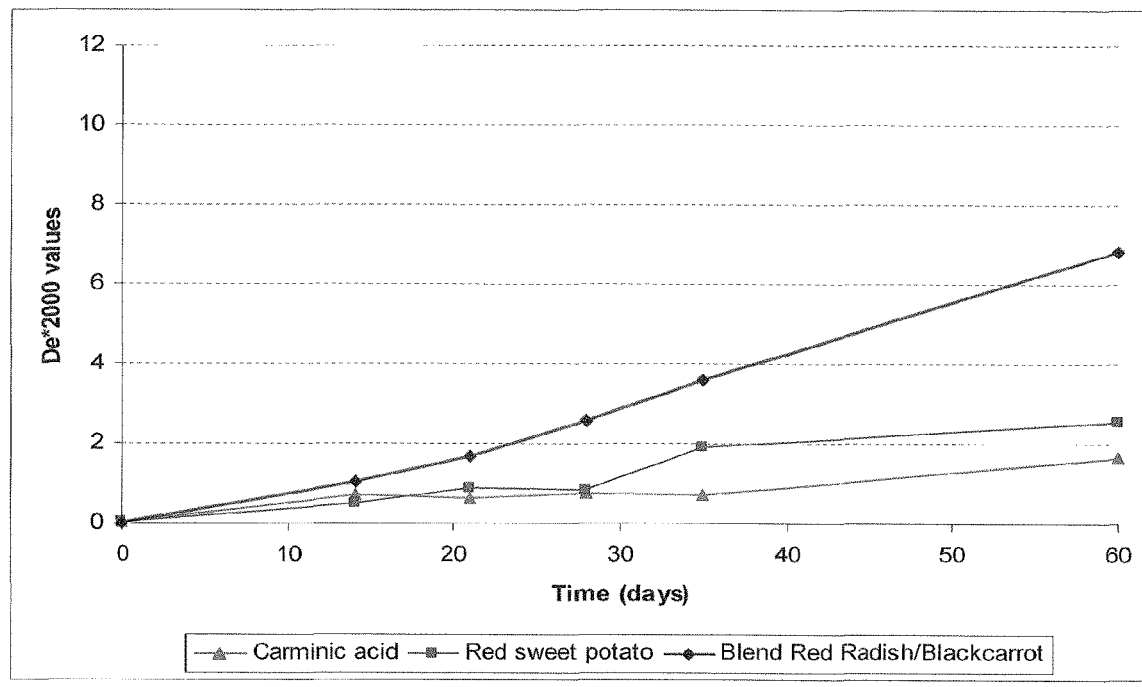
FIG. 9 Evolution of DE* 2000 during the 2-month storage of colored model beverage medium containing ascorbic acid under light exposure.
Figure 10:
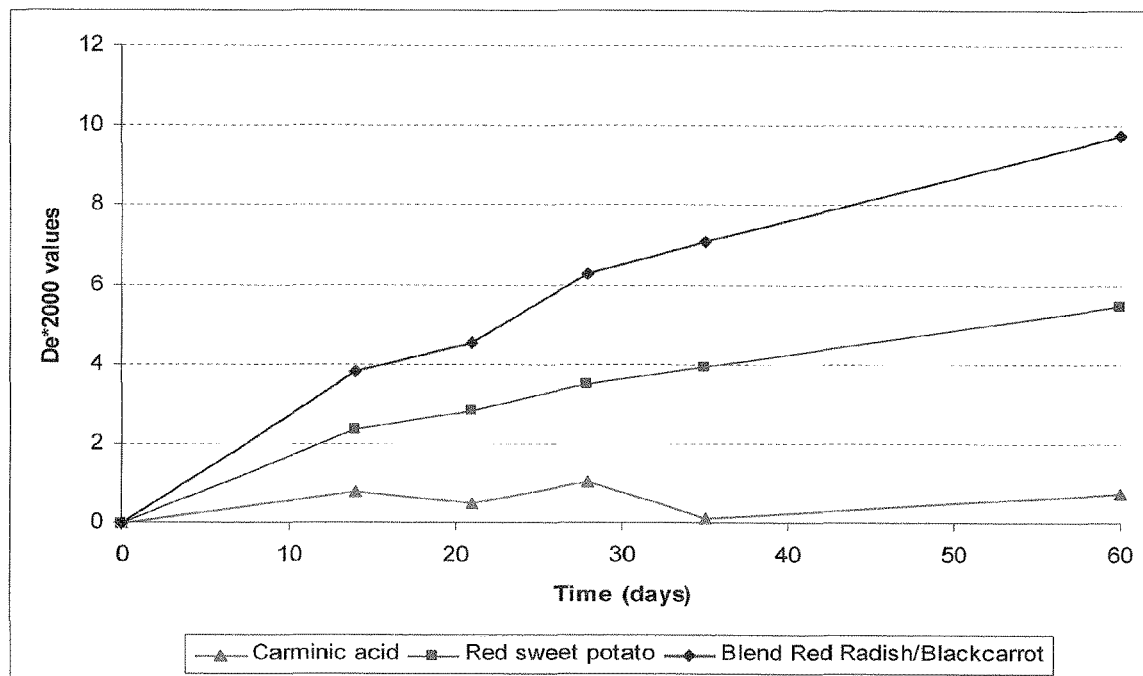
FIG. 10 Evolution of DE* 2000 during the 2-month storage of colored model beverage medium containing ascorbic acid under heat exposure.

The evolution of DE* 2000 during 2-month storage of colored model beverage medium under (i) light exposure and (ii) heat exposure is shown in FIGS. 9 and 10, respectively.

Beverage colored with RSWP is as stable as the one colored with carminic acid after 2-month light exposure in presence of ascorbic acid and the shift of shade is limited. Contrary thereto the beverage colored with rr/bc present a far lower stability to light exposure in presence of ascorbic acid.

Also, the beverage colored with RSWP, while presenting a not yet optimal stability such as carminic acid, provides a large improvement over rr/bc, considering the evolution of shade associated with the use of this traditional comparative colorant.

Example 7

Color Stability of a RSWP-Colored Fruit Preparation

RSWP concentrate is evaluated in a fruit preparation application for determining stabilities during storage of the fruit preparation itself and storage of a blend fruit preparation/white mass against a standard reference being used in this application.

Compared stabilities to pasteurization step of blends fruit preparation/white mass are also described.

A) Ingredients and Process

The model fruit preparation is a strawberry fruit preparation at pH 3.82 and 40.3° Brix. The colors were added directly into the fruit preparation at following dosages:
RSWP concentrate at 0.9%
Solubilized carmine lake at 0.56%

Model white mass is a commercial product containing 3.5% fat.

Colored fruit preparation was incorporated into the white mass at a weight ratio of 15/85 and the mixture was further pasteurized at 90° C. for 5 minutes.

B) Stability Evaluation

The colored fruit preparations were stored during one month at 10° C. and mixtures of fruit preparation/white mass were stored for 14 days in a cold room at 4° C. in the dark.

Colorimetric follow-up was done every week during two weeks for blends fruit preparation/white mass, and after one month storage for fruit preparations alone. Measurements were performed in Petri boxes using Datacolor SF 450 in reflection mode.

C) Results

Table 8 summarizes the shades of the blends fruit preparation/white mass colored with RSWP or the carmine lake reference at day 0 before the pasteurization step.

TABLE 8

|  | L* | C | h | DE* 2000 |
|---|---|---|---|---|
| RSWP | 75.52 | 15.37 | 10.94 |  |
| carmine lake | 73.61 | 21.75 | 4.93 | 4.52 |

The blend colored with RSWP is duller and more orange that the one colored with carmine lake.

Table 9 shows the stability of blends fruit preparation/white mass colored with RSWP or the carmine reference during the pasteurization step.

TABLE 9

|  | L* | C | h | DE* 2000 |
|---|---|---|---|---|
| RSWP before HT | 75.52 | 15.37 | 10.94 |  |
| RSWP after HT | 76.27 | 13.68 | 15.56 | 1.69 |
| Carmine lake before HT | 73.61 | 21.75 | 4.93 |  |
| Carmine lake after HT | 75.86 | 16.50 | 15.66 | 4.51 |

Blend fruit preparation/white mass colored with RSWP concentrate is far more stable through pasteurization compared to the blend colored with carmine lake and the variation of shade is acceptable (DE* 2000 below 2). This implies that the difference of shade between the two fruit preparation/white mass blends is reduced after pasteurization (DE* 2000=2.04).

Figure 11:
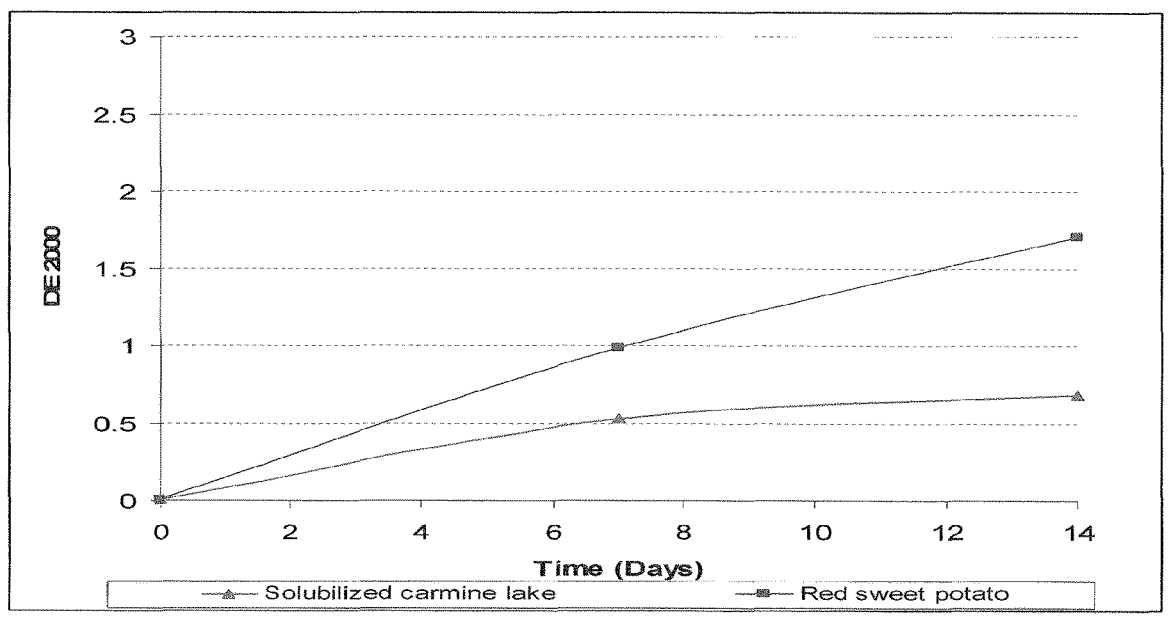
FIG. 11 Evolution of DE* 2000 during the 2-week storage of fruit preparation/white mass blends in cold room at 4° C.

FIG. 11 shows the evolution of DE* 2000 during the 2-week storage of fruit preparation/white mass blends in cold room at 4° C.

Blend fruit preparation/white mass colored with RSWP concentrate is less stable compared to the one colored with carmine lake under cold storage. Evolution of shade is visually detectable in former case but is considered as acceptable based on the DE 2000 value below 2.

Figure 12:
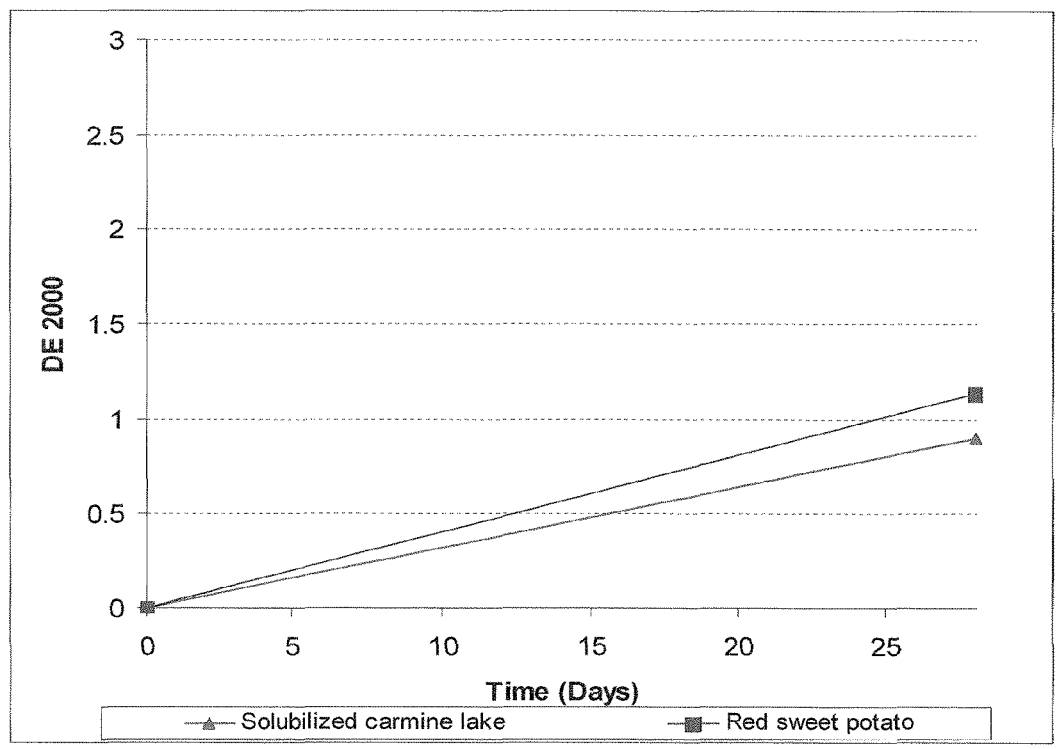
FIG. 12 Evolution of DE* 2000 during the 1-month storage of the colored fruit preparation.

FIG. 12 shows the evolution of DE* 2000 during the 1-month storage of the colored fruit preparation.

Fruit preparation colored with RSWP concentrate is almost as stable as the one colored with carminic acid after 1-month cold storage at 10° C. and no visual shift of shade is detected in both cases.

The invention claimed is:

1. A process for obtaining a composition, which is an anthocyanin-based colorant composition comprising 50-90 mol-%, based on the total amount of anthocyanins, of pelargonidin-based anthocyanins,
the process comprising the steps of:
(a) washing *Ipomoea batatas* sweet potato tubers or a juice or extract thereof with acidified water to obtain an acidified extract comprising anthocyanins; and
(b) filtering the acidified extract to obtain a food colorant composition comprising anthocyanins extracted from the sweet potatoes, wherein 50-90 mol % of the extracted anthocyanins present in the composition are pelargonidin-based anthocyanins extracted from the sweet potatoes, and wherein
(i) ≥70 mol-% of all anthocyanins are acylated with at least one benzoic acid; and
(ii) ≥20 mol-% of all anthocyanins are acylated with at least one hydroxycinnamic acid;

wherein the composition has a red color with a hue value H in the L*C*h* color system in the range of 10-30, measured at an L*-value of (70.0±0.1) in a 0.1 mol/l trisodium citrate dihydrate buffer at pH 3 in a 1 cm-length quartz cell using Spectraflash 650 (Datacolor) in transmission mode under D65 illuminant 10 Deg, wherein the composition contains no or only trace amounts of sulfur compounds, wherein the composition comprises, based on the total amount of anthocyanins, 5-55 mol-% of an acylated pelargonidin derivative (1) of the following formula (shown in the protonized, positively charged form:

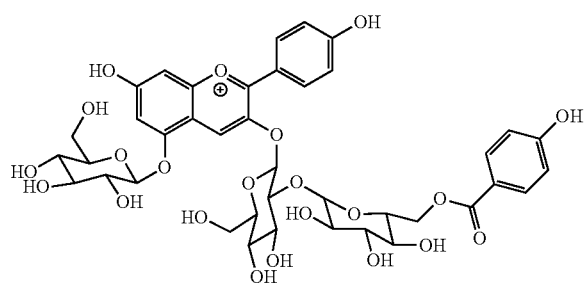

(1)

wherein the composition comprises, based on the total amount of anthocyanins, 3-60 mol-% of an acylated pelargonidin derivative (2) of the following formula, (shown in the protonized, positively charged form):

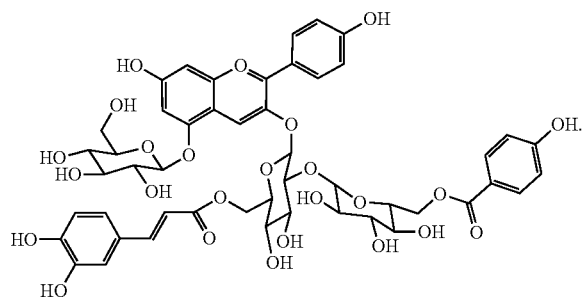

(2)

2. The process of claim 1, wherein 4-15 mol-% of all anthocyanins are peonidin-based anthocyanins.

3. The process of claim 1, and further including one of (a), (b) or (c):
(a) ≥80 mol-% of all anthocyanins are acylated with at least one benzoic acid;
(b) ≥85 mol-% of all anthocyanins are acylated with at least one benzoic acid;
(c) ≥90 mol-% of all anthocyanins are acylated with at least one benzoic acid.

4. The process of claim 1, and further including one of (a), (b), (c) or (d):
(a) up to 80 mol-% of all anthocyanins are acylated with at least one hydroxycinnamic acid;
(b) 25-75 mol-% of all anthocyanins are acylated with at least one hydroxycinnamic acid;
(c) 30-70 mol-% of all anthocyanins are acylated with at least one hydroxycinnamic acid;

(d) 35-65 mol-% of all anthocyanins are acylated with at least one hydroxycinnamic acid.

5. The process of claim 1, and further including one of (a), (b) or (c):
   (a) ≥80 mol-% of all anthocyanins are acylated with at least one benzoic acid;
   (b) ≥85 mol-% of all anthocyanins are acylated with at least one benzoic acid;
   (c) ≥90 mol-% of all anthocyanins are acylated with at least one benzoic acid.

6. The process of claim 1, and further including one of (a) or (b):
   (a) a color hue value H in the range of 13-27;
   (b) a color hue value H in the range of 18-24.

7. The process of claim 1, and further including one of (a), (b), (c) or (d):
   (a) the content of the pelargonidin derivative (1) is 10-30 mol-%;
   (b) the content of the pelargonidin derivative (1) is 15-45 mol-%;
   (c) the content of the pelargonidin derivative (1) is 20-40 mol-%;
   (d) the content of the pelargonidin derivative (1) is 25-35 mol-%.

8. The process of claim 1, and further including one of (a), (b), (c), (d) or (e):
   (a) the content of the pelargonidin derivative (2) is 5-58 mol-%;
   (b) the content of the pelargonidin derivative (2) is 8-56 mol-%;
   (c) the content of the pelargonidin derivative (2) is 13-54 mol-%;
   (d) the content of the pelargonidin derivative (2) is 18-52 mol-%;
   (e) the content of the pelargonidin derivative (2) is 23-50 mol-%.

9. The process of claim 1, and further including, for a colorant at 40-60% dry matter, one of (a), (b), (c) or (d):
   (a) an anthocyanin content, in terms of kuromanin equivalents of 2-30 mg/ml;
   (b) an anthocyanin content, in terms of kuromanin equivalents of 5-25 mg/ml;
   (c) an anthocyanin content, in terms of kuromanin equivalents of 8-21 mg/ml;
   (d) an anthocyanin content, in terms of kuromanin equivalents of 10-18 mg/ml.

10. The process of claim 1, wherein the composition is present in the form of a concentrate including one of (a), (b) or (c):
    (a) a dry matter content of 10-95 wt.-%;
    (b) a dry matter content of 15-85 wt.-%;
    (c) a dry matter content of 20-60 wt. %.

11. A method for coloring food which comprises adding the composition formed by the process of claim 1 as a food colorant to a food.

12. The method of claim 11, wherein the food is selected from beverages, fruit preparations, dairy, ice cream and confectionary.

13. The method of claim 12 where the food is a beverage.

* * * * *